US009314041B2

(12) United States Patent
Sashihara et al.

(10) Patent No.: US 9,314,041 B2
(45) Date of Patent: Apr. 19, 2016

(54) IMMUNE FUNCTION MODULATING AGENTS

(75) Inventors: Toshihiro Sashihara, Kanagawa (JP); Makoto Yamaguchi, Kanagawa (JP); Yoshitaka Nakamura, Kanagawa (JP); Shuji Ikegami, Kanagawa (JP); Seiko Narushima, Kanagawa (JP); Katsunori Kimura, Kanagawa (JP); Shinya Nagafuchi, Kanagawa (JP); Masaki Terahara, Kanagawa (JP)

(73) Assignee: MEIJI CO., LTD., Tokyo (JP)

( * ) Notice: Subject to any disclaimer, the term of this patent is extended or adjusted under 35 U.S.C. 154(b) by 2150 days.

(21) Appl. No.: 11/817,617

(22) PCT Filed: Feb. 23, 2006

(86) PCT No.: PCT/JP2006/303295
§ 371 (c)(1),
(2), (4) Date: Dec. 8, 2008

(87) PCT Pub. No.: WO2006/093022
PCT Pub. Date: Sep. 8, 2006

(65) Prior Publication Data
US 2009/0269321 A1    Oct. 29, 2009

(30) Foreign Application Priority Data
Mar. 3, 2005    (JP) .................. 2005-059460

(51) Int. Cl.
| C12N 1/20 | (2006.01) |
| A23C 19/032 | (2006.01) |
| A23C 9/123 | (2006.01) |
| A23L 1/30 | (2006.01) |
| A61K 35/747 | (2015.01) |
| C12R 1/225 | (2006.01) |

(52) U.S. Cl.
CPC ........... *A23C 19/0323* (2013.01); *A23C 9/1234* (2013.01); *A23L 1/3014* (2013.01); *A61K 35/747* (2013.01); *C12R 1/225* (2013.01)

(58) Field of Classification Search
None
See application file for complete search history.

(56) References Cited

U.S. PATENT DOCUMENTS

| 7,235,395 B2 | 6/2007 | Stadler et al. |
| 2005/0214270 A1 | 9/2005 | Yamamoto et al. |
| 2006/0088513 A1 | 4/2006 | Inoue et al. |

FOREIGN PATENT DOCUMENTS

| EP | 1239032 | 9/2002 |
| JP | H09259 A | 1/1997 |
| JP | H092959 A | 1/1997 |
| JP | 2003-095963 A | 4/2003 |
| JP | 2003-252772 A | 9/2003 |
| JP | 2003-253262 A | 9/2003 |
| JP | 2003-306436 A | 10/2003 |
| JP | 2004-018469 A | 1/2004 |
| JP | 2004-026729 A | 1/2004 |
| JP | 2004-091491 A | 3/2004 |
| JP | 2004-154035 A | 6/2004 |
| JP | 3585487 B1 | 8/2004 |
| JP | 2004-250337 A | 9/2004 |
| JP | 2004-528034 | 9/2004 |
| JP | 2004-315477 A | 11/2004 |
| WO | WO 02/086102 | 10/2002 |
| WO | WO 2004/003235 A2 | 1/2004 |
| WO | WO 2004/035072 A2 | 4/2004 |

OTHER PUBLICATIONS

Kitazawa et al., International Journal of Food Microbiology 65Ž2001. 149-162.*
Ho et al., Abstract of article in Allergy in Practice, vol. No. 338; pp. 983-988(2005) (English Abstract only).*
Kitazawa et al., FEMS Microbiology Letters 1994, vol. 120, Issue 3, 15 Jul. 1.*
Matsumura, et al., Animal Science and Technology [Anim. Sci. Technol.]. vol. 63, No. 11, pp. 1157-1159. 1992.*
Akahoshi et al., "Recent Topics in Allergic Disease: Overview," *Saishin Igaku*, 2003, vol. 58, No. 2, pp. 7-14.
ISE, "Recognition of food allergen in intestinal immune system," *Nourin Suisan Gifyutsu Kenkyu*, 2001, vol. 24, No. 5, pp. 9-14.
Kahou et al., "Allergy-sei Shikkan ni Taisuru Fukugo Probiotics Nyusankin no Yuekisei," *Allergy no Rinsho*, Feb. 20, 2006, vol. 26, No. 2, pp. 140-144.

(Continued)

*Primary Examiner* — Irene Marx
(74) *Attorney, Agent, or Firm* — Saliwanchik, Lloyd & Eisenschenk (57) ABSTRACT

A probiotic *lactobacillus* was discovered from lactobacilli of the *Lactobacillus* genus independently isolated from human adult feces. The probiotic *lactobacillus* was selected from other bacterial strains for: (1) being highly resistant to gastric acid/bile acid; (2) having a high promoting activity on IL-12 production from mouse derived spleen cells and a high Th1/Th2 balance-improving effect; (3) having a high ability to inhibit the production of antigen-specific IgE induced by intraperitoneally administering ovalbumin to BALB/c mice; (4) having a high ability to inhibit the production of antigen-specific IgE induced by orally administering a food antigen to C57BL/6N mice; (5) having a high Natural Killer cell-activating ability; (6) having a high IL-12 production-promoting activity on spleen cells and mesenteric lymph node cells derived from mice immunized with ovalbumin and a high Th1/Th2 balance-improving effect; and (7) having a high ability to suppress eosinophilia induced by a cedar pollen-extracted antigen. This discovery led to the completion of the present invention.

2 Claims, 3 Drawing Sheets

(56) References Cited

OTHER PUBLICATIONS

Kahou et al., "Probiotics Nyusankin Lactobacillus gasseri TMC0356 Kabu no Men'eki Shushoku oyobi Ko Allergy Sayo," *Allergy no Rinsho*, Nov. 20, 2005, vol. 25, No. 12, pp. 75-80.

Kalliomaki et al., "Probiotics in primary prevention of atopic disease: a randomised placebo-controlled trial," *The Lancet*, Apr. 7, 2001, vol. 357, No. 9262, pp. 1076-1079.

Naidu et al., "Probiotic Spectra of Lactic Acid Bacteria (LAB)," *Critical Reviews in Food Science and Nutrition*, Jan. 1999, vol. 39, No. 1, pp. 13-126.

Itoh et al., "*Lactobacillus gasseri* OLL2809 is effective especially on the menstrual pain in dysmenorrheal in endometriosis patients: randomized, double-blind, placebo-controlled study", *Cytotechnology*, 2011, vol. 63, No. 2, pp. 153-161.

Gotoh et al., "Efficacy of Oral Administration of a Heat-Killed *Lactobacillus gasseri* OLL2809 on Patients of Japanese Cedar Pollinosis with High Japanese-Cedar Pollen-Specific IgE", *Bioscience, Biotechnology and Biochemistry*, 2009, vol. 73, No. 9, pp. 1971-1977.

Yoshida et al., "*Lactobacillys gasseri* OLL2809 and its RNA suppress proliferation of $CD4^+$ T cells through MyD88-dependent signaling pathway", *Immunology*, 2011, vol. 133, No. 4, pp. 442-451.

* cited by examiner

IMMUNE FUNCTION MODULATING AGENTS

This application is a National Stage Application of International Application Number PCT/JP2006/303295, filed Feb. 23, 2006; which claims priority to JP 2005-059460, filed Mar. 3, 2005.

TECHNICAL FIELD

The present invention relates to agents for preventing and/or treating allergies, as well as dietary compositions for preventing and/or treating allergies that include these agents.

BACKGROUND ART

A sharp increase in allergic disorders, such as bronchial asthma, allergic rhinitis, and atopic dermatitis, has been observed in the past decades, and current estimates suggest that at least about one fifth of the population is affected with some type of allergic disease. Since most of the current agents for treating allergies are symptomatic, and in view of the increase in the number of affected patients and the side effects that accompany long-term uses, more effective treatments have been desired (Non-Patent Document 1).

Lactobacilli produce favorable flavoring substances and have an ability to produce anti-bacterial substances such as lactic acid and bacteriocins. As such, they have been consumed through fermented milk and the like from ancient times in different parts of the world. Accordingly, they are known to be very safe microorganisms. Moreover, a recent double blind placebo test showed that administration of *Lactobacillus rhamnosus* GG (*Lactobacillus rhamnosus* ATCC 53103), which is a type of *lactobacillus*, suppressed the incidence of atopic diseases in high risk children by about 50% (Non-Patent Document 2). Thus, use of lactobacilli appears to be an easy and effective method for preventing and/or treating allergies without accompanying side effects.

To date, various agents for preventing and/or treating allergies using lactobacilli have been proposed. However, regarding *Lactobacillus plantarum* CCRC 12944 and *Lactobacillus acidophilus* CCRC 14079 described in Patent Document 1, although the ability of interferon γ-production from cultured cells was evaluated upon selection of the *lactobacillus* strains, the preventive and/or therapeutic effects for allergies when the lactobacilli are actually taken up by animals was not investigated. Moreover, although it is desirable due to safety issues to isolate microorganism-based probiotics from humans (Non-Patent Document 3), this factor was not considered in the context of selection of the *lactobacillus* strains in the case of the *lactobacillus* strains described in Patent Documents 2 and 3 (*Lactococcus lactis* subsp. *lactis* G50 and *Lactobacillus paracasei* KW 3110). Regarding the lactobacilli described in Patent Documents 2 and 4 (*Lactococcus lactis* subsp. *lactis* G50, *Lactobacillus acidophilus* CP 1613. *Lactobacillus acidophilus* L 92, and *Lactobacillus fermentum* CP 34), the researchers therein failed to consider bacterial resistance to a low pH environment in the stomach or to the bile acid in the intestinal tract, both of which are properties of probiotics, when selecting the *lactobacillus* strains (Patent Documents 2 and 4). In addition, the *lactobacillus* disclosed in Patent Document 3 (*Lactobacillus paracasei* KW 3110) was selected by using as an index the production of antigen-specific IgE antibodies in the systemic immunity induced upon intraperitoneal administration of antigens to mice (Patent Document 3). However, it is unlikely that therapeutic effects against food allergies are appropriately evaluated by using the antibody production in systemic immunity as an index. Food taken orally is absorbed by the intestinal tract, and at the same time, recognized by an immune system unique to the intestinal tract, one that is distinct from the systemic immune system, referred to as gut-associated lymphatic tissue (GALT), and that normally induces an oral immune tolerance. On the other hand, in some cases, it induces the production of IgE antibodies, thus leading to the development of food allergy. The mechanism by which food, which normally should induce immune tolerance, induces food allergy is not sufficiently elucidated to date; however, it is contemplated that at least both the intestinal and systemic immune systems are involved in the development of food allergies. Thus, it is unlikely that an evaluation of allergy-preventing effects using the systemic immune system reflects the therapeutic effects against food allergies.

Thus, given the current situation with the existing lactobacilli, there remains room for improvement when preparing agents for preventing and/or treating allergies of interest, or dietary compositions for preventing and/or treating allergies.

Patent Document 1: Japanese Patent Application Kokai Publication No. (JP-A) 2004-91491 (unexamined, published Japanese patent application).

Patent Document 2: JP-A 2004-18469.

Patent Document 3: Japanese Patent No. 3585487.

Patent Document 4: JP-A 2004-26729.

Non-Patent Document 1: Akahoshi M, Tamari M, Shirokawa T, "Recent Topics in Allergic Diseases", Saishin Igaku, 58(2), pp. 7-14 (2003).

Non-Patent Document 2: Kalliomaki M, Salminen S, Arvilommi H, Kero P. Koskinen P. Isolauri E., "Probiotics in primary prevention of atopic disease: a randomised placebo-controlled trial", Lancet, 357(9262), pp. 1076-1079 (2001).

Non-Patent Document 3: Naidu A S, Bidlack W R, Clemens R A, "Probiotic spectra of lactic acid bacteria (LAB)", Critical Reviews in Food Science and Nutrition, 39(1), pp. 13-126 (1999).

Non-Patent Document 4: Ise W, "Progress in the studies of food allergy control; recognition of food allergen by the intestinal immune system", Agriculture, Forestry and Fisheries Technical Research Journal, 24(5), pp. 9-14 (2001).

DISCLOSURE OF THE INVENTION

Problems to be Solved by the Invention

Thus, a problem to be solved by the present invention is to select human intestine-derived lactobacilli that both possess an activity against allergies, such as food allergies, and have a high survival rate after administration, and to provide agents for preventing and/or treating allergies using such lactobacilli and/or treatment products thereof, as well as dietary compositions for preventing and/or treating allergies comprising the agents.

Means for Solving the Problems

The present invention was carried out to solve the above problems. To select the lactobacilli of interest for use in the context of agents for preventing and/or treating allergies, the present inventors developed a new set of criteria as described below, and performed dedicated operations for selection. Specifically, the present inventors performed dedicated research to select, from 273 strains of lactobacilli of the *Lactobacillus* genus independently isolated from human adult feces, a strain which: (1) is highly resistant to gastric acid/bile acid; (2) has a high IL-12 production-promoting activity in mouse-derived spleen cells and a high Th1/Th2 balance-improving effect; (3) has a high suppression effect on the antigen-specific IgE production induced by intraperitoneally administering ovalbumin to BALB/c mice; (4) has a high suppression effect on the antigen-specific IgE production induced by orally administering a food antigen (casein) to C57BL/6N mice; (5) has a high Natural Killer cell-activating ability; (6) has a high IL-12 production-promoting activity to spleen cells and mesenteric lymph node cells derived from mice immunized with ovalbumin and a high Th1/Th2 balance-improving effect; and (7) has a high ability to suppress eosinophilia induced by a cedar pollen-extracted antigen. As a result, the present inventors discovered *Lactobacillus gasseri* OLL2809 (Accession Number: NITE BP-72) as a probiotic *lactobacillus* that fulfills these conditions, and completed the present invention.

The effect described in the above (1) relates to the viability following administration. The *Lactobacillus gasseri* OLL2809 (Accession Number: NITE BP-72) possesses this effect and thus is expected to have a high viability in the intestinal lumen when administered as live bacteria in the form of an agent for preventing and/or treating allergies. The effects described in the above (2) to (7) relate to enhancement of Th1 response or suppression of Th2 response in vivo. A disruption of the balance between the helper T cells Th1 and Th2 is considered to be a cause of allergic diseases. The agents of the present invention for preventing and/or treating allergies and the dietary compositions of the present invention for preventing and/or treating allergies, which include the effects of (2) to (7) above, are useful in comprehensively improving a Th1/Th2 balance that has shifted toward Th2 and conditioning the immune functions. Thus, the agents of the present invention for preventing and/or treating allergies provide an allergy-preventing and/or -treating effect, even when the *Lactobacillus gasseri* OLL2809 (Accession Number: NITE BP-72) used is dead; moreover, a synergistic effect, such as an intestinal flora-improving effect, can be expected when the agents of the present invention are administered as live bacteria. In particular, the effect described in the above (4) is evaluated using a food allergy model. Thus, the agents of the present invention for preventing and/or treating allergies are expected to have a high therapeutic effect against food allergies.

Therefore, the present invention provides the following:

[1] an agent for preventing and/or treating allergies comprising *Lactobacillus gasseri* as an active ingredient;

[2] an agent for preventing and/or treating allergies comprising, as an active ingredient, a treatment product of *Lactobacillus gasseri* selected from the group consisting of a culture, concentrate, paste, spray-dried product, freeze-dried product, vacuum-dried product, drum-dried product, liquid, diluted product, and crushed product of the *lactobacillus;*

[3] the agent of [1] or [2] for preventing and/or treating allergies, wherein the prevention and/or treatment of allergies is associated with the suppression of antigen-specific IgE production;

[4] the agent of [1] or [2] for preventing and/or treating allergies, wherein the prevention and/or treatment of allergies is associated with the promotion of IL-12 production and improvement of the Th1/Th2 balance;

[5] the agent of [1] or [2] for preventing and/or treating allergies, wherein the prevention and/or treatment of allergies is associated with the activation of Natural Killer cells;

[6] the agent of [1] or [2] for preventing and/or treating allergies, wherein the prevention and/or treatment of allergies is associated with the suppression of eosinophilia;

[7] the agent of [1] or [2] for preventing and/or treating allergies, wherein the prevention and/or treatment of allergies is associated with at least one of the group consisting of: suppression of antigen-specific IgE production; promotion of IL-12 production and improvement of Th1/Th2 balance; activation of Natural Killer cells; and suppression of eosinophilia;

[8] the agent of any one of [1] to [7] for preventing and/or treating allergies, wherein the *Lactobacillus gasseri* is *Lactobacillus gasseri* OLL2809 deposited under the accession number NITE BP-72;

[9] a dietary composition for preventing and/or treating allergies, comprising an effective amount of the agent of any one of [1] to [8] for preventing and/or treating allergies;

[10] the dietary composition of [9] for preventing and/or treating allergies, which comprises a formula milk for infants, food such as powdered milk for infants, food such as powdered milk for nursing women, health-promoting food, food for sick people, or fermented milk;

[11] use of the agent of any one of [1] to [8] for preventing and/or treating allergies in the production of a dietary composition for preventing and/or treating allergies;

[12] the use of [11], wherein the dietary composition is selected from the group consisting of a formula milk for infants, food such as powdered milk for infants, food such as powdered milk for nursing women, health-promoting food, food for sick people, and fermented milk;

[13] a method for preventing and/or treating allergies which comprises the step of administering *Lactobacillus gasseri* or a treatment product thereof;

[14] a method for producing a dietary composition for preventing and/or treating allergies which comprises the step of using *Lactobacillus gasseri* or a treatment product selected from the group consisting of a culture, concentrate, paste, spray-dried product, freeze-dried product, vacuum-dried product, drum-dried product, liquid, diluted product, and crushed product thereof;

[15] *Lactobacillus gasseri* OLL2809 deposited under the accession number NITE BP-72;

[16] a treatment product of *Lactobacillus gasseri* OLL2809 deposited under the accession number NITE BP-72, wherein said *lactobacillus* treatment product is selected from the group consisting of a culture, concentrate, paste, spray-dried product, freeze-dried product, vacuum-dried product, drum-dried product, liquid, diluted product, and crushed product of the *lactobacillus;*

[17] a dietary composition or drink comprising *Lactobacillus gasseri* OLL2809 of [15] or the *lactobacillus* treatment product of [16]; and

[18] a pharmaceutical agent comprising *Lactobacillus gasseri* OLL2809 of [15] or the *lactobacillus* treatment product of [16].

EFFECTS OF THE INVENTION

The agents of the present invention for preventing and/or treating allergies possess a resistance to a low pH environment and to bile acid, an IL-12 production-promoting activity, a Th1/Th2 balance-improving effect, an ability to inhibit the production of IgE specific to food antigens in the serum, a Natural Killer cell-activating ability, and an eosinophilia-suppression ability, as confirmed in the Examples described below. Thus, the present invention enables the provision of novel agents for preventing and/or treating allergies, as well

BEST MODE FOR CARRYING OUT THE INVENTION

The present invention is described in detail below.

The present invention provides agents for preventing and/or treating allergies which include a *lactobacillus* as an active ingredient. The agents of the present invention for preventing and/or treating allergies include *Lactobacillus gasseri* as *lactobacillus*. While any *Lactobacillus gasseri* may be used, so long as it is effective in preventing and/or treating allergies, those types having a high viability after in vivo administration are preferred. One example of a *Lactobacillus gasseri* that can be used in the present invention is *Lactobacillus gasseri* OLL2809. Herein, 273 *lactobacillus* strains of the *Lactobacillus* genus independently isolated from adult human feces were examined using the following assays: (1) a gastric acid/bile acid resistance assay; (2) an assay for evaluating the IL-12 production-promoting effect to mouse-derived spleen cells and the Th1/Th2 balance-improving effect; (3) an assay for evaluating the suppression effect on antigen-specific IgE production induced by intraperitoneally administering oval-bumin to BALB/c mice; (4) an assay for evaluating the suppression effect on antigen-specific IgE production induced by orally administering a food antigen (casein) to C57BL/6N mice; (5) an assay for evaluating the ability to activate Natural Killer cells; (6) an assay for evaluating IL-12 production-promoting effect to spleen cells and mesenteric lymph node cells derived from mice immunized with ovalbumin and the Th1/Th2 balance-improving effect; and (7) an assay for evaluating the ability to suppress eosinophilia induced by cedar pollen. *Lactobacillus gasseri* OLL2809 (Accession Number: NITE BP-72; hereinafter also referred to as *L. gasseri* OLL2809) was then selected as a *lactobacillus* having a high activity in all areas tested and having an effect of preventing and/or treating allergies. Thus, the *lactobacillus* enables the provision of novel agents for preventing and/or treating allergies, as well as dietary compositions for preventing and/or treating allergies including such agents, which are effective in preventing and/or treating various allergies including food allergy.

The present inventors deposited this strain with the Incorporated Administrative Agency, National Institute of Technology and Evaluation, Patent Microorganisms Depositary. The specific content of the deposition is described below.

The present inventors deposited *Lactobacillus gasseri* OLL2809 with the Incorporated Administrative Agency, National Institute of Technology and Evaluation, Patent Microorganisms Depositary. The specific content of the deposition is detailed below:

(1) Name of depositary institution: The Incorporated Administrative Agency, National Institute of Technology and Evaluation, Patent Microorganisms Depositary.

(2) Contact: 2-5-8 Kazusakamatari, Kisarazu-shi, Chiba-ken, 292-0818.
Phone: 0438-20-5580

(3) Accession number: NITE BP-72

(4) Identification label: *Lactobacillus gasseri* OLL2809

(5) Date of original deposition: Feb. 1, 2005

(6) Date of transfer to the depositary under the Budapest Treaty: Jan. 18, 2006.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

*Lactobacillus gasseri* OLL2809 (Accession Number: NITE BP-72) is a Gram-positive *bacillus*. The morphology of colonies on the Lactobacilli MRS Agar, Difco, is round, light yellow, and flat. It possesses physiological characteristics such as homolactic fermentation, growth at 45° C., and fermentability for glucose, mannose, fructose, galactose, sucrose, cellobiose, lactose, and trehalose.

Media suitable for lactobacilli in general may also be used to culture the *Lactobacillus gasseri* OLL2809 strain (Accession Number: NITE BP-72). Thus, any medium containing, other than the main carbon source, a good extent of a nitrogen source, inorganic substances, and other nutrients can be used. Depending on the assimilating ability of the bacteria selected, lactose, glucose, sucrose, fructose, starch hydrolysate, molasses, and such can be used as the carbon source. Organic nitrogen-containing materials, such as casein hydrolysate, whey protein hydrolysate, and soybean hydrolysate, can be used as the nitrogen source. In addition, meat extracts, fish meat extracts, yeast extracts, and such can be used as growth-promoting agents.

Culture is preferably performed under anaerobic conditions; however, it may also be performed under microaerobic conditions, for example in the context of the commonly used stationary liquid culture. Known methods, such as the method of culturing under a nitrogen gas layer, can be applied to the anaerobic culturing, though other methods are contemplated as well. In general, the culture temperature preferably ranges between 30 and 40° C.; however, other temperature conditions may be used, so long as they allow the bacteria to grow. The pH of the medium is preferably maintained between 6.0 and 7.0 during culture; however, other pH conditions may be used, so long as the pH allows bacterial growth. Moreover, culture can also be carried out under batch culture conditions. In general, the duration of culture preferably ranges between 10 and 24 hours; however, other culture periods may be used, so long as they permit bacterial growth.

Other strains of *Lactobacillus gasseri* that can be used in the context of the present invention should possess characteristics similar to those of *Lactobacillus gasseri* OLL2809, such as Gram positivity and other physiological characteristics. Those skilled in the art can isolate such *Lactobacillus gasseri* from human feces and such based on known physiological characteristics. The effect of preventing and/or treating allergies can be confirmed performing, for example, assays that evaluate the IL-12 production-promoting effect and the Th1/Th2 balance-improving effect; the suppressive effect on antigen-specific IgE production (intraperitoneal or oral administration of the antigens); the Natural Killer cell-activating ability; and the ability to suppress eosinophilia. Specific confirmatory methods are described in the Examples below. In addition, the viability after in vivo administration can be confirmed by a gastric acid/bile acid resistance assay, and more particularly, by the method described in the Examples herein. Culture can also be performed by methods similar to those described above for *Lactobacillus gasseri* OLL2809.

The agents of the present invention for preventing and/or treating allergies can include the aforementioned *Lactobacillus gasseri* in various forms, for example as a *lactobacillus* suspension, a *lactobacillus* culture (bacteria, culture supernatant (comprising culture medium components)), or a *lactobacillus* fermentation product (*lactobacillus* beverages, sour milk, yoghurt, etc.).

The agent of the present invention for preventing and/or treating allergies may include the above *Lactobacillus gasseri* as is or as a *lactobacillus* treatment product, in which some treatment has been carried out to the *Lactobacillus gasseri*. Examples of *lactobacillus* treatment products suitable for use as agents of the present invention for preventing and/or treating allergies include lactobacilli, materials containing lactobacilli, concentrates of fermented milk, pastes, dried products (at least one selected from spray-dried products, freeze-dried products, vacuum-dried products, and drum-dried products), liquids, diluted materials, and crushed materials. Live, moist, or dried bacteria can be appropriately used. Dead bacteria to which sterilization, such as a heat-sterilization treatment, an irradiation sterilization treatment, or a crushing treatment had been performed may be used as well. The bacteria can also be added to pharmaceuticals and/or food/drink that meet biological standard, such as powdered milk, and are applicable to a variety of pharmaceuticals and/or food/drink, regardless of the forms of the pharmaceuticals and/or food/drink.

The agents of the present invention for preventing and/or treating allergies are effective in preventing allergies and in decreasing the symptoms of (treating) allergies in humans and animals, if orally administered alone or after mixing with other elements that can be commonly used for pharmaceuticals and food, or if used in combination with other compounds, microorganisms, or such that have anti-allergic activity. They can be used for preventing and/or treating allergies. It has been revealed that a Th1/Th2 balance that has shifted toward the Th2 side is a cause of allergic diseases such as atopic dermatitis and allergic rhinitis (Hopkin J. M. The rise of atopy and links to infection. Allergy 57:5-9 (2002); Prescott S. L., Macaubas C., Smallacombe T., Holt B. J., Sly P. D., and Holt P. G. Development of allergen-specific T-cell memory in atopic and normal children. Lancet 353:196-200 (1999); Shirakawa T., Enomoto T., Shimizu S., and Hopkin J. M. The inverse association between tuberculin responses and atopic disorder. Science 275:77-79 (1997)). The agents of the present invention for preventing and/or treating allergies have the effects, to cells obtained from allergy model animals, of: (1) increasing the production of IL-12, which is produced from dendritic cells and acts to induce the differentiation of Th1 helper cells; and (2) suppressing the production of Th2 cytokines (IL-4). Therefore, they are expected to have the effect of adjusting a Th1/Th2 balance that had shifted to the Th2 side toward the Th1 side. Moreover, NK cells comprise the property of being activated by IL-12 and Th1 cytokines (IL-2). The agents of the present invention for preventing and/or treating allergies have been shown to have an NK cell-activating effect, and the Th1/Th2 balance-improving effect has also been demonstrated from this side as well. Furthermore, the agents of the present invention for preventing and/or treating allergies have an eosinophilia-suppressing effect, which further supports the effect of preventing and/or treating allergies. Eosinophils are leukocytes that increase as one of the inflammatory cells in type I allergies, and are also known to increase subsequent to a parasitic infection. Known diseases associated with a high level of eosinophils include allergic rhinitis, allergic conjunctivitis, bronchial asthma, atopic dermatitis, food allergies, hypersensitivity to foreign proteins, parasitic infections, sudden lung eosinophilia syndrome, and such (Laboratory medicine: selection and interpretation of clinical examinations, edited by Howanitz J. H. and Howanitz P. J., translation supervised by Kohno K., Ishiyaku Publishers Inc. pp. 583 (1995)). Moreover, since IgE production is also increased in type I allergies, the products of present invention that have the effect of suppressing eosinophilia and IgE production can be expected to drive a decrease in the symptoms of allergic rhinitis, allergic conjunctivitis, bronchial asthma, atopic dermatitis, food allergies, hypersensitivity to foreign proteins, anaphylactic reactions, and such. The allergy types, symptoms, and diseases to which the agents of the present invention for preventing and/or treating allergies can be applied are not particularly limited; however, examples include type I to type IV allergies, food allergies, pollen allergies, atopic dermatitis, bronchial asthma, allergic conjunctivitis, allergic rhinitis, allergic gastroenteritis, anaphylactic reactions, drug allergies, urticaria, serum sickness, hemolytic anemia, contact dermatitis, myasthenia gravis, Goodpasture's syndrome, and glomerulonephritis. Applicable allergens are not particularly limited either; examples include food (wheat, barley, oats, rye, buckwheat, eggs, milk, cheese, peanuts, rice, corn, foxtail millet, proso millet, Japanese millet, soy beans, potatoes, yams, garlic, onions, carrots, parsleys, celeries, tomatoes, oranges, peaches, apples, kiwi fruit, melons, strawberries, bananas, walnuts, sesame, matsutake mushrooms, abalones, squids, salmon caviars, shrimps, crabs, salmons, mackerels, horse mackerels, sardines, cods, squids, octopuses, scallops, beef, chicken, pork, gelatin, etc), animals (dogs, cats, mice, rats, pigeons, and such, and their skin, hair, feces, feather, etc.), insects (moths, butterflies, chironomids, hornets, and such, and their secretion products and scales), ticks, parasites (Anisakis, ascarids, etc.), plants (cedars, cypresses, ragweeds, gramineous plants, mugwort, lacquer trees, alders, and such, and the pollens, saps, and such of these plants), molds, dust, house dust, rubber, metals, chemical substances, and pharmaceuticals.

*Lactobacillus* culture media after culture can be used "as is", as concentrates after concentration, or after further drying the concentrates, as the agents of the present invention for preventing and/or treating allergies. The concentration of bacteria is not particularly limited, but is preferably $4 \times 10^{10}$ cells/g or higher for concentrated solutions, and $5 \times 10^{11}$ cells/g or higher for dried products.

The amount of the agents of the present invention for preventing and/or treating allergies mixed in pharmaceuticals or food/drink differs depending on its configuration, dosage form, symptoms, body weight, use, and such; thus it is not limited in particular. However, the agents can be mixed, for example, at a content of 0.001 to 100% (w/w), preferably at a content of 0.01 to 100% (w/w), and more preferably at a content of 0.1 to 100% (w/w).

The amount of the pharmaceuticals or food/drink containing the agents of the present invention for preventing and/or treating allergies that is taken per day varies with age, symptoms, body weight, use, and such; thus, it is not particularly limited. However, the pharmaceuticals or food/drink can be taken at 0.1 to 10000 mg/kg body weight, and preferably at 0.1 to 1000 mg/kg body weight.

The agents of the present invention for preventing and/or treating allergies can be configured both as a pharmaceutical and as a food/drink. For example, prevention and/or treatment of various allergies are expected through their direct administration as pharmaceuticals, or through direct injection as food with nutrient function claims or special-use food, such as food for specified health use. Moreover, they can be added to various food and drink (e.g., milk, processed milk, milk beverages, soft drinks, fermented milk, yoghurt, cheese, bread, biscuits, crackers, pizza crusts, ice creams, candy, formula milk, fluid diet, food for sick people, food such as powdered milk for infants, food such as powdered milk for nursing women, nutritive food, etc), and this can be ingested.

Food and drink containing the agents of the present invention for preventing and/or treating allergies can be used after mixing with water, proteins, sugars, lipids, vitamins, minerals, organic acids, organic bases, fruit juices, flavors, and such. Examples of proteins include animal or plant proteins, such as whole powdered milk, powdered skim milk, partially-skimmed milk, casein, whey powder, whey proteins, whey protein concentrates, whey protein isolates, α-casein, β-casein, κ-casein, β-lactoglobulin, α-lactalbumin, lactoferrin, soy bean proteins, chicken egg proteins, and meat proteins as well as their hydrolysates; and various milk-derived components such as butter, whey minerals, cream, whey, non-protein nitrogen, sialic acid, phospholipids, and lactose. Examples of sugars include processed starch (dextrin, soluble starch, British starch, oxidized starch, starch ester, starch ether, etc) and dietary fibers. Examples of lipids include animal oils, such as lard and fish oils, as well as their separated oils, hydrogenated oils, and interesterified and/or transesterified oils; and vegetable oils, such as palm oil, safflower oil, corn oil, rapeseed oil, coconut oil, as well as their separated oils, hydrogenated oils, and interesterified and/or transesterified oils. Examples of vitamins include vitamin A, carotenes, vitamin B group, vitamin C, vitamin D group, vitamin E, vitamin K group, vitamin P, vitamin Q, niacin, nicotinic acid, pantothenic acid, biotin, inositol, choline, and folic acid. Examples of minerals include calcium, potassium, magnesium, sodium, copper, iron, manganese, zinc, and selenium. Examples of organic acids include malic acid, citric acid, lactic acid, and tartaric acid. When producing food/drink containing the agents of the present invention for preventing and/or treating allergies, these components may be synthesized or naturally derived, and/or food abundantly including these components may also be used as source material. Moreover, two or more of these components can be used in combination.

When the agents of the present invention for preventing and/or treating allergies are used to produce dietary compositions and pharmaceuticals, production methods known to those skilled in the art can be used. Those skilled in the art can appropriately combine the steps of mixing the *Lactobacillus gasseri* bacteria of the present invention or treatment products with other components, shaping, sterilizing, fermenting, firing, drying, cooling, granulating, packing, and such to produce desired food and pharmaceuticals.

Moreover, when the *Lactobacillus gasseri* of the present invention is used to produce a variety of milk products, the desired milk products can be produced by methods known to those skilled in the art. For example, in the case of yoghurt, yoghurt can be produced through the steps of: preparing a starter using the *Lactobacillus gasseri* of the present invention; adding the starter to pre-treated milk and culturing it; cooling; flavoring; packing; and such. Cheese can be produced, for example, through the steps of: lactic fermentation after adding the *Lactobacillus gasseri* of the present invention as a starter to milk to which a pretreatment such as sterilization had been carried out; producing cheese curd by adding rennet; cutting the curd; discarding whey; adding salt; and maturation. Alternatively, in the above-described production of the various types of milk products, other lactobacilli may be used as the starter in place of the *Lactobacillus gasseri* of the present invention, and the *Lactobacillus gasseri* bacteria of the present invention or the treatment products may be added during a production step.

The agents of the present invention for preventing and/or treating allergies can be administered in various configurations, when used as pharmaceuticals. Examples of configurations include oral administrations using tablets, capsules, granules, powders, syrups, etc. These various formulations can be formulated using, in addition to the main agent, known auxiliary agents that can generally be used in the technical field of pharmaceutical formulation, such as excipients, binding agents, disintegrants, lubricants, odor-improving agents, solubilizing agents, suspending agents, and coating agents, according to standard methods.

All prior art references cited herein are incorporated by reference into this description.

EXAMPLES

Herein below, the present invention will be specifically described with reference to Examples, but it should not be construed as being limited thereto.

Example 1

Gastric Acid Resistance Assay and Bile Acid Resistance Assay 273 lactobacillus strains of the Lactobacillus genus isolated from human feces were subjected to the following assays:

1) Gastric Acid Resistance Assay:

Lactobacillus bacteria were washed twice with physiological saline, and 1 ml of the lactobacillus suspension solution was added to 9 ml of filter sterilized artificial gastric fluid (NaCl (0.2%) and pepsin (1:5000, Tokyo Chemical Industry) (0.35%)) (pH 2). After aerobic culture at 37° C. for 2 hours, 1 ml was taken from this artificial gastric fluid containing the lactobacilli and added to 9 ml of phosphate buffer (67 mM, pH 6.5) to terminate the reaction. The number of live bacteria before and after contact with the artificial gastric fluid was measured using the Lactobacilli MRS Agar (Difco), and the viability rate (%) and gastric acid resistance (%) were calculated.

2) Bile Acid Resistance Assay:

10 μl of lactobacilli precultured twice (37° C., 18 hours) in Lactobacilli MRS Broth were inoculated in 5 ml Lactobacilli MRS Broth containing 0.9% Bacto-Oxgall (Difco), and anaerobically incubated at 37° C. After 18 hours of culture, the turbidity (OD650) of the medium at a wavelength of 650 nm was measured, and the value was used as an index for bile acid resistance.

The results of the gastric acid resistance assay and bile acid resistance assay are shown in Table 1. As a result of examining the gastric acid resistance and bile acid resistance for 273 lactobacillus strains of the Lactobacillus genus, the tendency that strains with a high gastric acid resistance have a low bile acid resistance, and strains with a high bile acid resistance have a low gastric acid resistance was observed. When viewed according to the bacterial types, Lactobacillus gasseri (hereinafter also referred to as L. gasseri) had a high resistance to gastric acid, whereas Lactobacillus plantarum (hereinafter also referred to as L. plantarum) had a high bile acid resistance. Bile acid resistance of most bacterial strains was 1.0 or lower. Six strains of L. plantarum, two strains of Lactobacillus crispatus (hereinafter also referred to as L. crispatus), two strains of Lactobacillus amylovorus (hereinafter also referred to as L. amylovorus), one strain of Lactobacillus casei (hereinafter also referred to as L. casei), and one strain of Lactobacillus brevis (hereinafter also referred to as L. brevis) were selected as bacterial strains having a high bile acid resistance. Moreover, gastric acid resistance was 0.5% or lower for most bacterial stains. Among the bacterial strains with a high gastric acid resistance (0.5% or higher), eight strains of L. gasseri were selected as bacterial strains with a relatively high bile acid resistance (0.1 or higher).

TABLE 1

| | GASTRIC ACID RESISTANCE (%) | BILE ACID RESISTANCE (OD650) |
|---|---|---|
| L. plantarum MEP170401 | 0.14 | 9.31 |
| L. plantarum MEP170402 | 0.15 | 10.79 |
| L. plantarum MEP170403 | 0.02 | 8.7 |
| L. plantarum MEP170404 | 0.03 | 6.55 |
| L. plantarum MEP170405 | 0.03 | 4.42 |
| L. plantarum MEP170406 | 0.39 | 7.45 |
| L. gasseri MEP170407 | 22.41 | 0.13 |
| L. gasseri MEP170408 | 24.91 | 0.12 |

TABLE 1-continued

| | GASTRIC ACID RESISTANCE (%) | BILE ACID RESISTANCE (OD650) |
|---|---|---|
| L. gasseri MEP170409 (OLL2809) | 0.86 | 0.31 |
| L. gasseri MEP170410 | 2.10 | 0.24 |
| L. gasseri MEP170411 | 20.78 | 0.45 |
| L. gasseri MEP170412 | 0.80 | 0.43 |
| L. gasseri MEP170413 | 6.21 | 0.12 |
| L. gasseri MEP170414 | 0.53 | 0.14 |
| L. crispatus MEP170415 | 0.12 | 1.76 |
| L. crispatus MEP170416 | 0.12 | 3.69 |
| L. amylovorus MEP170417 | 0.06 | 2.71 |
| L. amylovorus MEP170418 | 0.04 | 2.49 |
| L. brevis MEP170419 | 0.00 | 1.48 |
| L. casei MEP170420 | 0.00 | 1.31 |

Table 1 shows the results for the gastric acid resistance (%) and bile acid resistance (OD650) assays for the 20 selected lactobacillus strains of the Lactobacillus genus.

Example 2

Preparation of Freeze-dried lactobacillus Bacteria

The 20 lactobacillus strains of the Lactobacillus genus selected in Example 1 were precultured twice (37° C., 18 hours) in Lactobacilli MRS Broth. The precultures were inoculated in the sane medium at 1% and cultured at 37° C. for 18 hours. Bacteria were collected, then washed twice with physiological saline and once with sterile distilled water, sterilized by heating at 75° C. for 60 minutes, and freeze-dried. Freeze-dried bacterial powder was used in the in vitro assays and animal administration experiments below.

Example 3

Assays for Evaluating the Effect of Promoting IL-12 Production from Mouse-derived Spleen Cells and the Th1/Th2 Balance-improving Effect The gastric acid-resistant and bile acid-resistant 20 lactobacillus strains of the Lactobacillus genus which were selected in Example 1 were evaluated by the methods below.

20 μg of ovalbumin (hereinafter also referred to as OVA, Wako Pure Chemical Industries) and 2 mg of aluminum hydroxide (Wako Pure Chemical Industries) were intraperitoneally administered to six-week-old male BALB/c mice (n=4, Japan SLC). Eight days later, the spleens were removed. Spleen cells from which erythrocytes have been removed were resuspended at $2.5 \times 10^6$ cells/ml in 10% FCS-RPMI 1640 medium (Gibco) containing 1 μg/ml of heat-treated lactobacilli prepared in Example 2 and 100 μg/ml of OVA, and cultured in a 5% $CO_2$ incubator for six days. Type strains of the Lactobacillus genus (L. plantarum JCM $1149^T$, L. gasseri JCM $1131^T$, L. crispatus JCM $1185^T$, L. amylovorus JCM $1126^T$), and type strains of other bacteria (Bifidobacterium bifidum JCM $1255^T$ (hereinafter also referred to as B. bifidum JCM $1255^T$), Bifidobacterium longum JCM $1217^T$ (hereinafter also referred to as B. longum JCM $1217^T$), Lactococcus delbrueckii subsp. lactis JCM $1248^T$ (hereinafter also referred to as L. delbrueckii subsp. lactis JCM $1248^T$), Enterococcus faecalis IFO 3971 (hereinafter also referred to as E. faecalis IFO 3971), Bacteroides vulgatus JCM $5826^T$ (hereinafter also referred to as B. vulgatus JCM $5826^T$), and Escherichia coli JCM $1649^T$ (hereinafter also referred to as E. coli JCM $1649^T$)) were used as comparative controls. Among the above bacterial strains, those indicated with JCM in the bacterial strain name are type strains obtained from the independent administrative agency, Institute of Physical and Chemical Research, BioResource Center, Microbe Division/Japan Collection of Microorganisms; and those indicated with IFO in the bacterial strain name are type strains obtained from the Institute for Feiiiientation. Strains indicated with MEP in the bacterial name are bacterial strains held by Meiji Dairies Corporation. Moreover, controls were prepared similarly as described above, except that microorganisms were not added. IFN-γ, IL-12, and IL-4 in culture supernatants were measured by ELISA (BD OptEIATM ELISA set, Becton Dickinson). The significant difference over the control group was tested by Student's t-test with significant level at 5%. The results are shown in Table 2.

*tarum*, and the like, including *L. gasseri* MEP170409 (*Lactobacillus gasseri* OLL2809 (Accession Number: NITE BP-72) were revealed to have a strong IL-12 production-promoting activity and Th1/Th2 balance-improving effect.

*L. plantarum* MEP170402, *L. gasseri* MEP170407, *L. gasseri* MEP170409 (*Lactobacillus gasseri* OLL2809 (Accession Number: NITE BP-72)), and *L. gasseri* MEP170413, which are four strains with a strong IL-12 production-promoting activity and Th1/Th2 balance-improving effect, were selected in this way.

TABLE 2

|  | IL-12 (pg/ml) | | IFN-γ (ng/ml) | | IL-4 (pg/ml) | |
| --- | --- | --- | --- | --- | --- | --- |
|  | AVERAGE | SD | AVERAGE | SD | AVERAGE | SD |
| CONTROL | 0 | 0 | 0.4 | 0.2 | 265 | 75 |
| *L. plantarum* JCM 1149$^T$ | 39 | 26 | 10.6* | 3.4 | 102* | 53 |
| *L. plantarum* MEP170401 | 4907* | 1160 | 30.4* | 7.0 | 34* | 11 |
| *L. plantarum* MEP170402 | 4723* | 971 | 26.9* | 10.4 | 35* | 6 |
| *L. plantarum* MEP170403 | 4602* | 869 | 20.5* | 4.5 | 36* | 11 |
| *L. plantarum* MEP170404 | 4748* | 950 | 25.5* | 9.3 | 38* | 9 |
| *L. plantarum* MEP170405 | 4966* | 965 | 24.4* | 4.0 | 15* | 11 |
| *L. plantarum* MEP170406 | 3407* | 602 | 27.8* | 7.3 | 27* | 9 |
| *L. gasseri* JCM 1131$^T$ | 3721* | 1338 | 28.0* | 5.2 | 43* | 14 |
| *L. gasseri* MEP170407 | 4521* | 1101 | 27.5* | 5.8 | 35* | 4 |
| *L. gasseri* MEP170408 | 1213* | 405 | 19.5* | 6.3 | 64* | 20 |
| *L. gasseri* MEP170409 (OLL2809) | 2990* | 617 | 19.8* | 6.5 | 61* | 19 |
| *L. gasseri* MEP170410 | 3039* | 627 | 30.9* | 3.6 | 35* | 9 |
| *L. gasseri* MEP170411 | 1667* | 285 | 29.7* | 6.8 | 46* | 14 |
| *L. gasseri* MEP170412 | 43 | 77 | 7.8* | 1.1 | 140 | 31 |
| *L. gasseri* MEP170413 | 3662* | 582 | 24.8* | 3.0 | 40* | 12 |
| *L. gasseri* MEP170414 | 557* | 147 | 18.7* | 5.4 | 49* | 15 |
| *L. crispatus* JCM 1185$^T$ | 41 | 47 | 2.7* | 0.7 | 169 | 43 |
| *L. crispatus* MEP170415 | 0 | 0 | 0.8 | 0.5 | 176 | 62 |
| *L. crispatus* MEP170416 | 0 | 0 | 1.6* | 0.4 | 216 | 80 |
| *L. amylovorus* JCM 1126$^T$ | 742* | 292 | 31.0* | 6.8 | 22* | 6 |
| *L. amylovorus* MEP170417 | 0 | 0 | 5.6* | 1.2 | 259 | 156 |
| *L. amylovorus* MEP170418 | 0 | 0 | 4.7* | 2.4 | 196 | 57 |
| *L. brevis* MEP170419 | 0 | 0 | 2.0 | 1.1 | 224 | 57 |
| *L. casei* MEP170420 | 0 | 0 | 4.0* | 1.7 | 181 | 81 |
| *B. bifidum* JCM 1255$^T$ | 0 | 0 | 0.2 | 0.2 | 200 | 69 |
| *B. longum* JCM 1217$^T$ | 0 | 0 | 1.8* | 0.7 | 362* | 110 |
| *L. delbrueckii* subsp. *lactis* JCM 1248$^T$ | 1032* | 234 | 17.1* | 2.4 | 34* | 16 |
| *E. faecalis* IFO 3971 | 4816* | 1324 | 31.1* | 7.4 | 47* | 29 |
| *B. vulgatus* JCM 5826$^T$ | 43 | 50 | 1.8* | 0.7 | 235 | 60 |
| *E. coli* JCM 1649$^T$ | 225* | 120 | 18.0* | 1.6 | 46* | 21 |

‡: p < 0.05 (vs CONTROL, STUDENT'S t-TEST)

Table 2 shows the effects of the 20 *lactobacillus* strains of the *Lactobacillus* genus selected in Example 1 on production of cytokines (IL-12, IFN-γ, and IL-4) by spleen cells. The average value±standard deviation for each measured value is shown. *: p<0.05 (vs. control. Student's t-test).

13 out of 30 strains significantly (p<0.05) and strongly promoted IL-12 production, this phenomenon was primarily observed with *L. plantarum*, *L. gasseri*, and such. However, even among the same bacterial types, some had a strong IL-12-inducing activity, whereas some had no activity, and the activity was bacterial strain-specific and was not dependent on the bacterial types. In addition, a positive correlation (n=31, r=0.8047, p<0.01) and a negative correlation (n=31, r=−0.6544, p<0.01) with the IL-12 production level were observed for IFN-γ and IL-4, respectively. Thus, the bacterial strains that strongly induce IL-12 production have a high IFN-γ production-promoting effect and a high IL-4 production-suppressing effect, and improved the Th1/Th2 balance. From the above results, specific strains of *L. gasseri*, *L. plan-*

Example 4

Assay for Evaluating the Suppressive Effect on the Antigen-specific IgE Production Induced by Intraperitoneal Administration of Ovalbumin to BALB/c Mice The four *lactobacillus* strains of the *Lactobacillus* genus selected in Example 3 were evaluated by the method described below.

Figure 1:
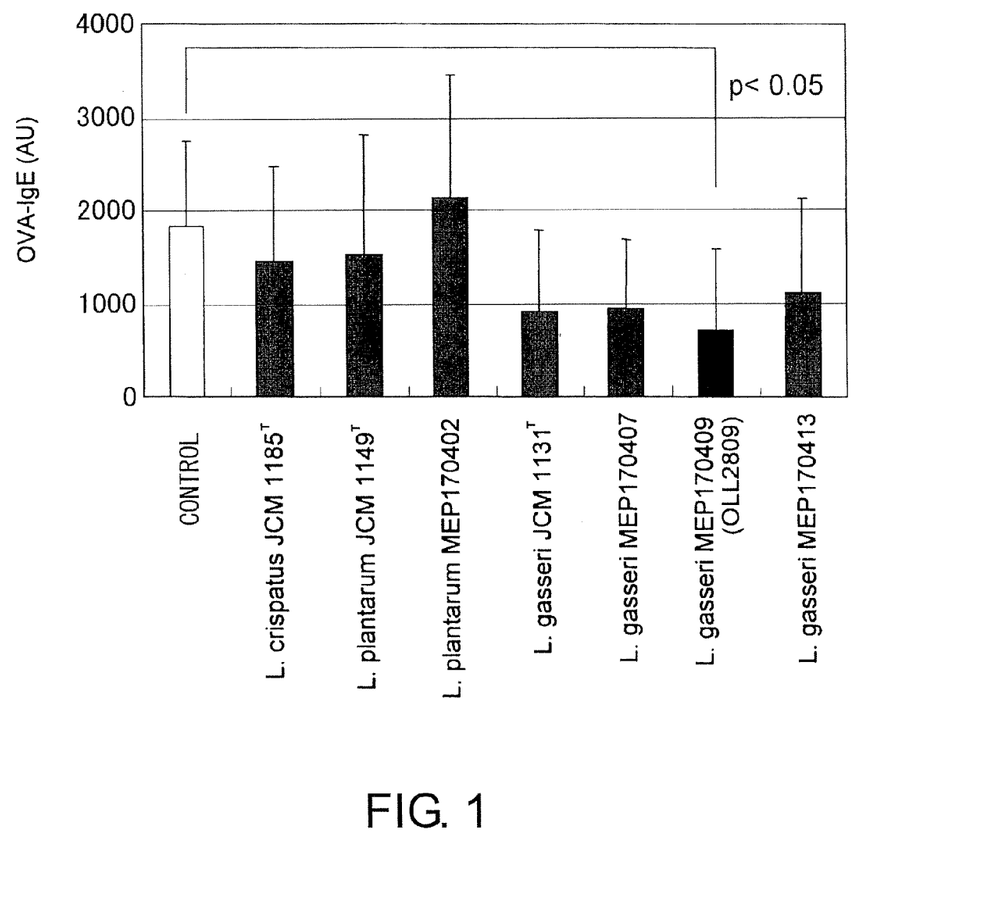
FIG. 1 depicts the IgE-suppressing effect of orally administered gastric acid/bile acid-resistant lactobacilli of the *Lactobacillus* genus to intraperitoneally OVA-administered BALB/c allergy models. The average values±standard deviation (n=10) for the concentration of anti-OVA specific IgE antibodies (AU) in the control group (control), the test bacteria-administered groups, and comparative control groups (*L. crispatus* JCM 1185$^T$, *L. plantarum* JCM 1149$^T$, *L. gasseri* JCM 1131$^T$) are shown. p<0.05 (vs. control; Fisher's PLSD test).

0.2 µg/g body mass of OVA (Wako Pure Chemical Industries) and 0.1 mg/g body mass of aluminum hydroxide (Wako Pure Chemical Industries) were intraperitoneally administered to six-week-old male BALB/c mice (n=10 for each group, Japan SLC) (primary immunization). Two weeks later, a secondary immunization with OVA and aluminum hydroxide was carried out under similar conditions. During the 21 days from the primary immunization to one week after the secondary immunization, mice were subjected to free feeding of MF feed (Oriental Yeast Co.) containing various freeze-dried *lactobacillus* powder prepared in Example 2 at 0.1%. The suppressive effect on the production of anti-OVA specific IgE for the lactobacilli *L. plantarum* MEP170402, *L. gasseri* MEP170407, *L. gasseri* MEP170409 (*Lactobacillus gasseri* OLL2809 (Accession Number: NITE BP-72)), and *L. gasseri* MEP170413 was examined using, as comparative controls, *L. crispatus* JCM 1185$^T$ and *L. plantarum* JCM 1149$^T$, both of which, as shown in the results of Example 3, have a low IL-12-inducing activity, and *L. gasseri* JCM 1131$^T$, which has a high IL-12-inducing activity (see Example 3). The controls were fed with MF feed alone. Blood was collected one week after secondary immunization, and the concentration of anti-OVA specific IgE antibodies in the serum was measured by ELISA. As for the anti-OVA specific IgE antibody concentration, 20 µg of OVA and 2 mg of aluminum hydroxide were peritoneally administered twice at intervals of two weeks to six-week-old male BALB/c mice (Japan SLC), and the concentration of anti-OVA specific IgE antibodies comprised in the serum one week later was defined as 10,000 AU. Measurement of the concentration of anti-OVA specific IgE antibodies was performed using biotinylated rat anti-mouse monoclonal IgE antibodies (BD biosciences), and streptavidin-horseradish peroxidase (BD biosciences) according to the method of Ito et al. (Ito K., Inagaki-Ohara K., Murosaki S., Nishimura H., Shimokata T., Torii S., Matsuda T., and Yoshikai Y., Murine model of IgE production with a predominant Th2-response by feeding protein antigen without adjuvants. Eur. J. Immunol., 27:3427-3437 (1997)) with modification. The results were analyzed by one-way analysis of variance, followed by multiple comparison test using Fisher's PLSD test with significant level at 5%. The results are shown in FIG. 1.

No difference was observed for *L. crispatus* JCM 1185$^T$ and *L. plantarum* JCM 1149$^T$ as compared with the control. No difference was observed between *L. plantarum* MEP170402, which showed a high IL-12-inducing effect in vitro, and the control either. Among the tested strains, *Lactobacillus gasseri* OLL2809 (Accession Number: NITE BP-72) had the strongest suppressive effect on anti-OVA specific IgE production, and the observed decrease was significant compared to control (p<0.05). *L. gasseri* JCM 1131$^T$ and *L. gasseri* MEP170407 showed a tendency of suppressing antigen-specific IgE induction (p=0.072, and p=0.064, respectively). *L. plantarum* did not show any IgE production-suppression effect in vivo, whereas *L. gasseri* generally had a strong effect. From the above, *Lactobacillus gasseri* OLL2809 (Accession Number: NITE BP-72) were revealed to have a strong suppressive effect on anti-OVA specific IgE production.

Example 5

Assay for Evaluating the Suppressive Effect on Antigen-specific IgE Production Induced by Oral Administration of a Food Antigen to C57BL/6N Mice The 20 gastric acid/bile acid-resistant *lactobacillus* strains of the *Lactobacillus* genus which were selected in Example 1 were evaluated by the method below.

Three-week-old female C57BL/6N mice (control, n=20; test bacteria-administered groups, n=10; CLEA Japan) were subjected to free feeding for two weeks of feed having the composition shown in Table 3 to which various freeze-dried *lactobacillus* powders prepared in Example 2 have been added at 0.1% (test bacteria-administered groups). Controls were fed with feed having the composition shown in Table 3. All groups were fed with MF feed (Oriental Yeast Co.) during the subsequent seven weeks. Furthermore, the test bacteria-administered groups were subjected to free feeding for two weeks of feed having the composition shown in Table 3 to which various freeze-dried *lactobacillus* powders prepared in Example 2 have been added at 0.1%, and the control group was subjected to free feeding for two weeks of feed having the composition shown in Table 3. After feeding was terminated, whole blood was collected, and rat intracutaneous acute anaphylactic reaction (hereinafter also referred to as passive cutaneous anaphylaxis (PCA) reaction) assays were carried out using the serum from each mouse, and the positive rate for anti-casein specific IgE was compared between the control and the test bacteria-administered groups.

TABLE 3

| INGREDIENTS | BLENDED QUANTITY (WEIGHT %) |
|---|---|
| CASEIN (ARACID, NZMP) | 22.0% |
| SUCROSE | 5.0% |
| CORN STARCH | 60.3% |
| CELLULOSE POWDER | 3.0% |
| SOYBEAN OIL | 5.0% |
| AIN-76 VITAMIN MIX | 1.0% |
| AIN-76 MINERAL MIX | 3.5% |
| CHOLINE BITARTRATE | 0.2% |
| TOTAL | 100.0% |

The AIN-76 vitamin mix and AIN-76 mineral mix shown in Table 3 indicate the vitamin mix and mineral mix blended in AIN-76, which is a standard purified feed for nutrition studies in mice and rats presented in 1977 by the American Institute of Nutrition (AIN).

[Determination of IgE Production-suppression Effect by PCA Reaction]

For PCA reaction, seven-week-old male SD rats (Japan SLC) were shaved on the back and 25 µl of mouse serum were injected intradermally. Twenty-four hours after intradermal injection of serum to mice, 0.5 ml of a solution comprising 2 mg/ml of casein and 1% of Evans Blue (Wako Pure Chemical Industries) was injected into a tail vein of rats. Thirty minutes after intravenous injection of casein and Evans Blue, the presence or absence of a leak of the Evans Blue dye under the back skin was judged visually, and those for which a dye leak was observed were determined to be PCA reaction-positive. The number of PCA reaction-positives in each group was determined and a significant difference test according to a chi-square test with significant level at 5% was carried out with the numbers of PCA reaction-positives for the control group and the test bacteria-administered groups. The results are shown in Table 4.

TABLE 4

| TEST GROUPS | NUMBER OF PCA REACTION-POSITIVES/TESTED NUMBER |
|---|---|
| CONTROL | 18/20 |
| *L. plantarum* MEP170401 | 8/10 |
| *L. plantarum* MEP170402 | 7/10 |
| *L. plantarum* MEP170403 | 7/10 |
| *L. plantarum* MEP170404 | 7/10 |
| *L. plantarum* MEP170405 | 8/10 |
| *L. plantarum* MEP170406 | 9/10 |
| *L. gasseri* MEP170407 | 8/10 |
| *L. gasseri* MEP170408 | 10/10 |
| *L. gasseri* MEP170409 (OLL2809) | 5/10* |
| *L. gasseri* MEP170410 | 10/10 |

TABLE 4-continued

| TEST GROUPS | NUMBER OF PCA REACTION-POSITIVES/TESTED NUMBER |
|---|---|
| L. gasseri MEP170411 | 8/10 |
| L. gasseri MEP170412 | 9/10 |
| L. gasseri MEP170413 | 6/10 |
| L. gasseri MEP170414 | 8/10 |
| L. crispatus MEP170415 | 7/10 |
| L. crispatus MEP170416 | 7/10 |
| L. amylovorus MEP170417 | 5/10* |
| L. amylovorus MEP170418 | 10/10 |
| L. brevis MEP170419 | 9/10 |
| L. casei MEP170420 | 6/10 |

*p < 0.05 (vs CONTROL, CHI-SQUARE TEST)

Table 4 shows the effect of oral administration of the 20 lactobacillus strains of the Lactobacillus genus selected in Example 1 on IgE production in food allergy mice. The number of PCA reaction-positives/tested number are shown. *: p<0.05 (vs. control, chi-square test).

18 out of 20 animals were positive in the control group. On the other hand, the number of positives was 5 out of 10 for the Lactobacillus gasseri OLL2809 (Accession Number: NITE BP-72)-administered group and L. amylovorus MEP170417-administered group; a significant suppression (p<0.05) was observed. No significant effect was observed with the other strains.

From the above, oral administration of Lactobacillus gasseri OLL2809 (Accession Number: NITE BP-72) to mouse models of food allergy induced by oral administration of casein was shown to have a highly suppressive effect on antigen-specific IgE production compared to other bacterial strains.

Example 6

Assay for Evaluating Natural Killer Cell-activating Ability

The 20 gastric acid/bile acid-resistant lactobacillus strains of the Lactobacillus genus selected in Example 1 were evaluated by the method below.

Figure 2:
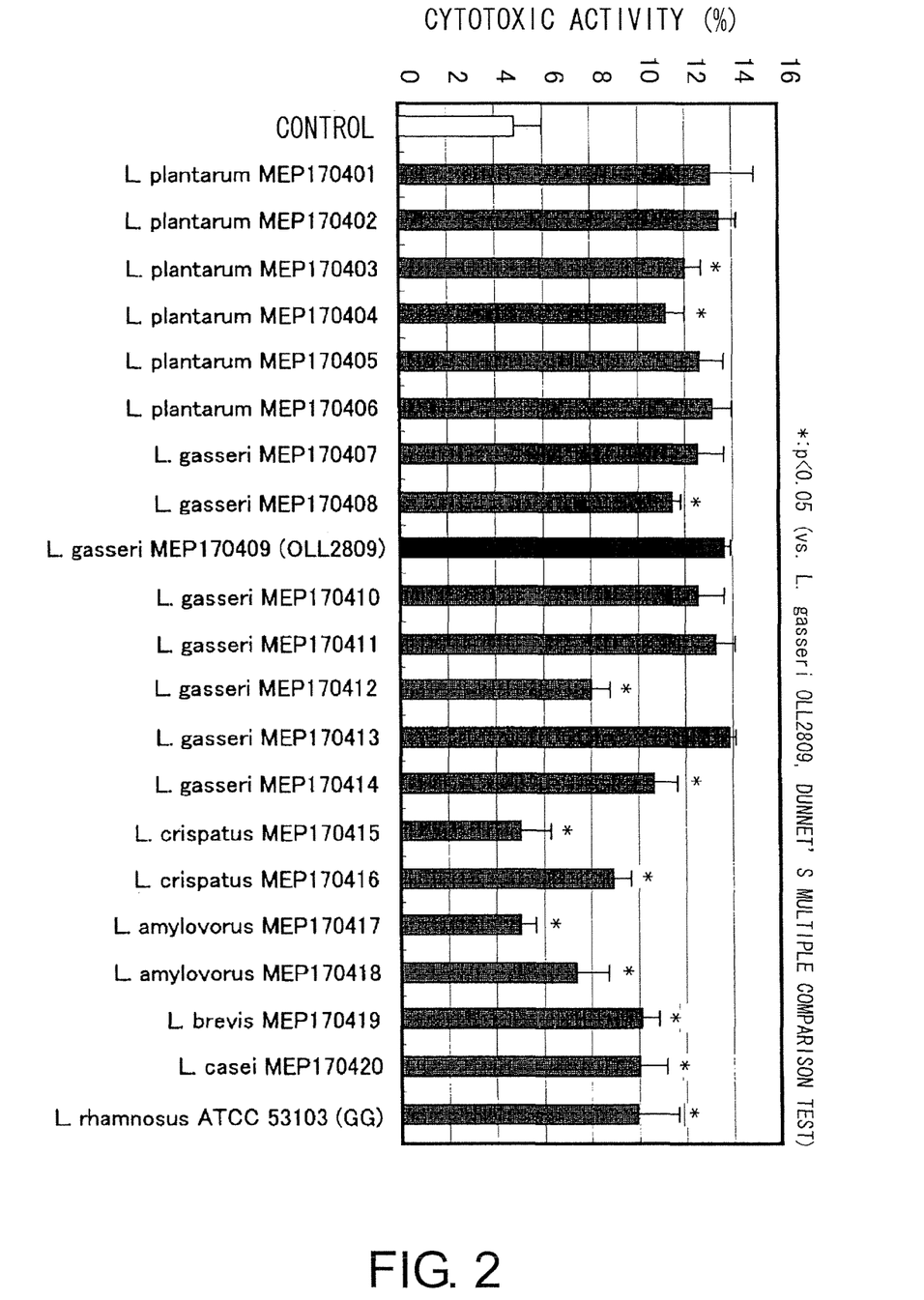
FIG. 2 depicts the effect of the gastric acid/bile acid-resistant lactobacilli of the *Lactobacillus* genus on the Natural Killer activity of murine spleen cells. The average values±standard deviation (n=4) for the cytotoxic activity rate (%) of the control, the test bacteria-administered groups, and the positive control (*L. rhamnosus* ATCC 53103) are shown. *: p<0.05 (vs. *L. gasseri* OLL2809; Dunnett's multiple comparison test).

Spleen cells were collected from 10 week-old female BALB/c mice (Japan SLC). The YAC-1 cell line (a cell line highly sensitive to Natural Killer cells) was used as the target cells. Calcein (Dojindo) was added as a fluorescent label for YAC-1 cells at a final concentration of 20 μM to cells at $1\times10^6$ cells/ml, this was left still for 1 hour, then washed. $5\times10^5$ spleen cells in a liquid volume of 100 μl and 0.20 μg of the various freeze-dried lactobacillus powders prepared in Example 2 in a liquid volume of 50 μl (final concentration: 1.3 μg/ml) were added per well in 96-well plates, and incubated overnight. Then, $1\times10^4$ of the above-described fluorescently-labeled YAC-1 cells in a liquid volume of 50 μl (ratio of spleen cells:YAC-1 cells=50:1) were added thereto, and this was incubated for 3 hours. A similar procedure was performed for the control wells but with no addition of freeze-dried lactobacillus powder to the spleen cells. Moreover, L. rhamnosus ATCC 53103 (Lactobacillus rhamnosus GG strain) was used as a positive control. Following the culture, the fluorescence intensity of culture supernatants was measured (Excitation: 485 nm, Emission: 535 nm), and the values were designated the test measured values. Further, the fluorescence intensities of culture supernatants from cultures of spleen cells alone or YAC-1 cells alone were designated spleen cell spontaneous measured value and YAC-1 spontaneous measured value, respectively. The fluorescence intensity obtained when YAC-1 cells were cultured alone and cells were destroyed by the addition of Triton X-100 (Wako Pure Chemical Industries) was designated the total measured value. These values were applied to the Equation below to calculate the cytotoxic activity. Statistical analyses were performed using Dunnett's multiple comparison test, and tests for significant difference over Lactobacillus gasseri OLL2809 (Accession Number: NITE BP-72) were carried out with significant level at 5%. The results are shown in FIG. 2.

$$|\text{CYTOTOXIC ACTIVITY}(\%) = \frac{\text{TEST} - Y - S}{\text{TOTAL} - Y} \times 100 \quad \text{[Equation 1]}$$

In the above equation, Test, Total, S, and Y indicate the test measured value, the total measured value, the spleen cell spontaneous measured value, and the YAC-1 spontaneous measured value, respectively.

Among the examined 20 strains, the cytotoxic activity increased particularly when bacterial strains belonging to L. plantarum or L. gasseri were added. Specimens to which Lactobacillus gasseri OLL2809 (Accession Number: NITE BP-72) were added showed a significantly (p<0.05) higher cytotoxic activity compared to positive control specimens.

From the above, Lactobacillus gasseri OLL2809 (Accession Number: NITE BP-72) were shown to have a high Natural Killer cell-activating ability in systems that use spleen cells.

Taken together, the Lactobacillus gasseri OLL2809 (Accession Number: NITE BP-72) was discovered as a lactobacillus that shows a strong activity in all of the following assays: (1) gastric acid/bile acid resistance assay; (2) assay for evaluating the effect of promoting IL-12 production from mouse-derived spleen cells and the Th1/Th2 balance-improving effect; (3) assay for evaluating the suppression of antigen-specific IgE induced by intraperitoneal administration of ovalbumin to BALB/c mice; (4) assay for evaluating the ability to inhibit the production of antigen-specific IgE induced by oral administration of a food antigen to C57BL/6N mice; and (5) assay for evaluating Natural Killer cell-activating ability.

Example 7

Assay for Evaluating the Th1/Th2 Balance-improving Effect by Spleen Cells and Mesenteric Lymph Node Cells Using BALB/c Mice to which OVA was Intraperitoneally Administered Two lactobacillus strains of the Lactobacillus genus selected in Example 3 were evaluated by the following method.

Figure 3:
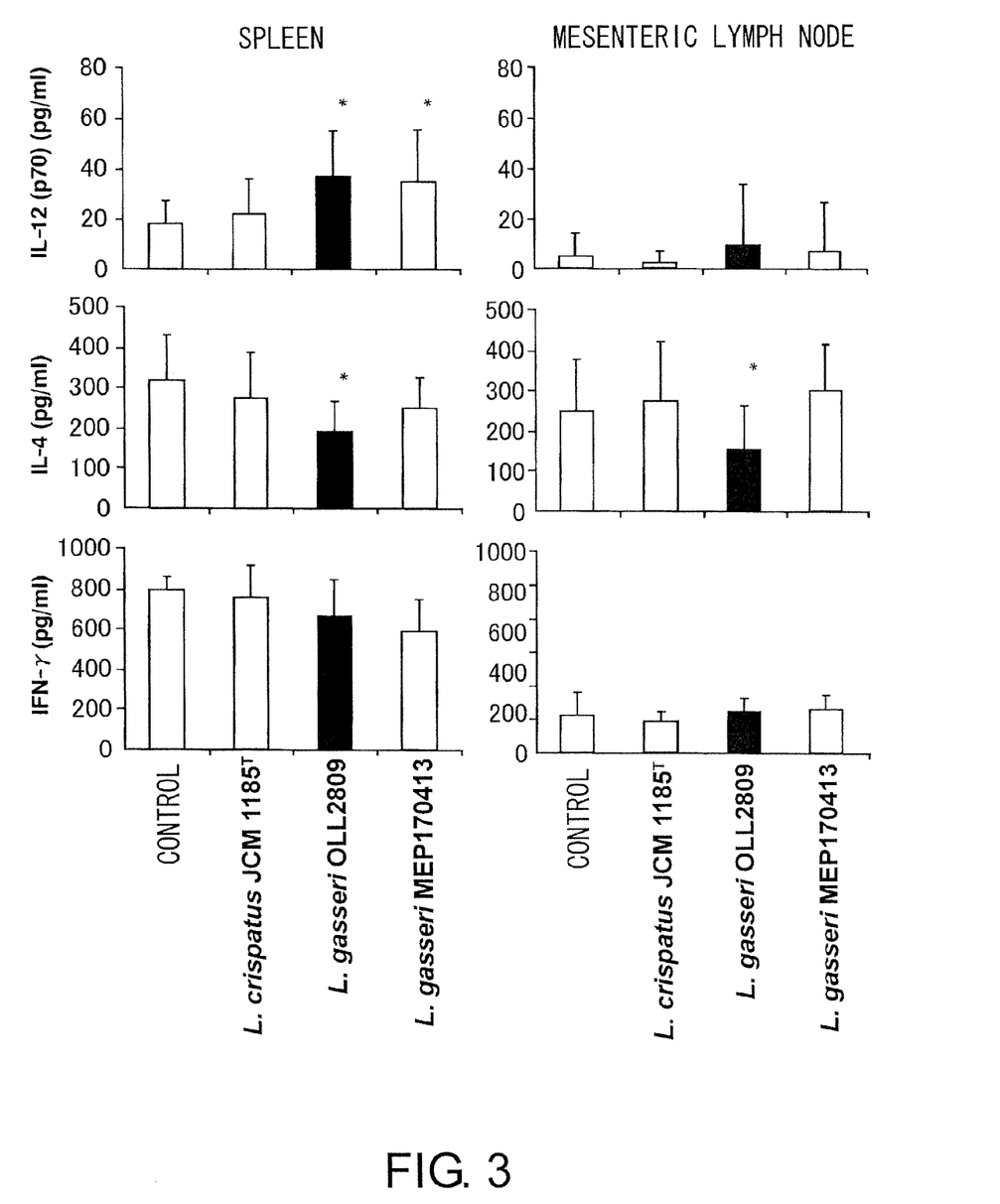
FIG. 3 depicts cytokine production by spleen cells and mesenteric lymph node cells prepared from intraperitoneally OVA-administered BALB/c allergy model mice to which lactobacilli of the *Lactobacillus* genus were orally administered. The average values±standard deviation (n=10) for each cytokine in the control group, the comparative control group (*L. crispatus* JCM 1185$^T$), and the test bacteria-administered groups (*L. gasseri* OLL2809, *L. gasseri* MEP170413) are shown. *: p<0.05 (vs. control; Fisher's PLSD test).

0.2 μg/g body mass of OVA (Wako Pure Chemical Industries) and 0.1 mg/g body mass of aluminum hydroxide (Wako Pure Chemical Industries) were intraperitoneally administered to six-week-old male BALB/c mice (n=10 for each group, Japan SLC) (primary immunization). Two weeks later, a secondary immunization with OVA and aluminum hydroxide was carried out under similar conditions. During the 21 days from the primary immunization to one week after the secondary immunization, mice were subjected to free feeding of MF feed (Oriental Yeast Co.) containing various freeze-dried lactobacillus powders prepared in Example 2 at 0.1%. One week after secondary immunization, spleen cells and mesenteric lymph node cells were prepared from each group of mice. After erythrocytes were removed, spleen cells were seeded in 24 well plates at a concentration of 2.5×10⁶ cells/well, and mesenteric lymph node cells were seeded in 48 well plates at a concentration of 1.25×10⁶ cells/ well. Both cells were incubated in 10% FCS-RPMI 1640 medium (Gibco, 1 ml/well) comprising 100 μg/ml of OVA for two or six days in a 5% $CO_2$ incubator at 37° C. For both cells, the concentration of IL-12 (p70) in the culture supernatant after two days of cultivation, and the concentration of IFN-γ and IL-4 in the culture supernatant after six days of cultivation were measured by ELISA (BD OptEIATM ELISA set, Becton Dickinson). The results were analyzed by one-way analysis of variance, followed, if justified with a significant level at 5%, by multiple comparison test using Fisher's PLSD test with significant level at 5%.

The lactobacilli used were *L. gasseri* OLL2809 (Accession Number: NITE BP-72) and *L. gasseri* MEP170413, which were selected based on the results of Example 3, and L crispatus JCM 1185$^T$, which showed a low IL-12-inducing activity, as a comparative control. Controls were fed with MF feed alone. The results are shown in FIG. 3.

A significant (p<0.05) increase as compared to control was observed for the production of IL-12 (p70) from spleen cells in the *L. gasseri* OLL2809 (Accession Number: NITE BP-72)-administered group. Furthermore, a significant (p<0.05) decrease as compared to control was observed in the amount of IL-4 produced from spleen cells and mesenteric lymph node cells in the *L. gasseri* OLL2809 (Accession Number: NITE BP-72)-administered group.

In the case of *L. gasseri* MEP170413, a significant (p<0.05) increase was observed for the amount of IL-12 (p70) produced from spleen cells; however, no effect was observed for the IL-4 production of both the spleen cells and the mesenteric lymph node cells. No change was observed in the cytokine production of these cells with *L. crispatus* JCM 1185$^T$. From the above, it was discovered that, when orally administered to BALB/c mice to which OVA was intraperitoneally administered, *L. gasseri* OLL2809 (Accession Number: NITE BP-72) has an effect of improving the Th1/Th2 balance of spleen cells and mesenteric lymph node cells.

Example 8

Assay for Evaluating Eosinophilia-suppressing Effect Using a Model of Eosinophilia Induced by a Cedar Pollen-extracted Antigen Antigen sensitization was carried out by administering 0.2 ml/body of a cedar pollen-extracted antigen solution (comprising Cry j 1 at 0.4 μg/ml) on day 0, 1, 6, 8, and 14 from the start of the experiment to seven-week-old female BALB/c mice (n =9 or 10 per group, Japan SLC) subcutaneously in the back. Cedar pollen-extracted antigen solution was administered by a similar method on day 20 to induce eosinophilia. Sensitization was not carried out on the negative control group, and only the induction was carried out. Water (control) or various doses (0.5, 1.0, or 2.0 mg) of *L. gasseri* OLL2809 (Accession Number: NITE BP-72) prepared according to Example 2 were forcefully administered into stomach for each group every day for 21 days from the start of experiment. The group composition is shown below. 5 ml of phosphate buffered saline containing 1% FCS was intraperitoneally injected on day 21, and intraperitoneal cells were collected. The total cell concentration of intraperitoneal cells was measured using an automated blood cell counter (F-800, Sysmex), then intraperitoneal cell smears were prepared using a cell collection centrifuge (Cytospin 3, Shandon). Intraperitoneal cells were stained with the Hemacolor quick staining kit (Merck), and the number of eosinophils was counted under the microscope. The eosinophil suppression rate was determined using the equation below.

[Equation 2]

$$\text{EOSINOPHIL SUPPRESSION RATE}(\%) = \left[1 - \frac{\begin{pmatrix} \text{EOSINOPHIL NUMBER} \\ \text{OF INDIVIDUAL MICE} \\ \text{OF EACH GROUP} \end{pmatrix} - \begin{pmatrix} \text{MEAN EOSINOPHIL} \\ \text{NUMBER OF} \\ \text{THE NEGATIVE} \\ \text{CONTROL GROUP} \end{pmatrix}}{\begin{pmatrix} \text{MEAN EOSINOPHIL} \\ \text{NUMBER} \\ \text{OF THE} \\ \text{CONTROL GROUP} \end{pmatrix} - \begin{pmatrix} \text{MEAN EOSINOPHIL} \\ \text{NUMBER OF} \\ \text{THE NEGATIVE} \\ \text{CONTROL GROUP} \end{pmatrix}}\right] \times 100$$

TABLE 5

| GROUPS | SENSI-TIZATION | INDUCTION | ADMINISTERED OLL2809 AMOUNT (mg/BODY/DAY) |
|---|---|---|---|
| CONTROL GROUP | ○ | ○ | 0 (WATER ONLY) |
| NEGATIVE CONTROL GROUP | X | ○ | 0 (WATER ONLY) |
| 0.5 mg GROUP | ○ | ○ | 0.5 |
| 1.0 mg GROUP | ○ | ○ | 1.0 |
| 2.0 mg GROUP | ○ | ○ | 2.0 |

By sensitization/induction using cedar pollen-extracted antigen, the total cell concentration, eosinophil concentration, and eosinophil ratio (eosinophil number/total cell number) in the collected peritoneal fluid significantly increased (p<0.01) in the control group as compared with the negative control group. In the group to which *L. gasseri* OLL2809 (Accession Number: NITE BP-72) was administered, the eosinophil ratio was significantly suppressed (p<0.05 or 0.01) with any administered dose as compared with the control group. Moreover, no significant difference was observed for the total cell concentration of the collected peritoneal lavage fluid in all the sensitized/induced groups. However, the eosinophil concentration showed a significant low value (p<0.05) as compared to the control group in just the 2 mg-administered group, and eosinophilia was significantly suppressed (p<0.05), at about 44%.

From the above results, the OLL2809 was revealed to suppress eosinophilia through oral administration into eosinophilia model mice.

TABLE 6

| GROUP | TOTAL CELL CONCENTRATION (×10⁵ cell/ml) | EOSINOPHIL CONCENTRATION (×10⁵ cell/ml) | EOSINOPHIL RATIO (%) | EOSINOPHIL SUPPRESSION RATE (%) |
|---|---|---|---|---|
| CONTROL GROUP | 16.7 ± 2.1 | 4.30 ± 0.70 | 25.5 ± 1.6 | 0.0 ± 17.0 |
| NEGATIVE CONTROL GROUP | 8.5 ± 1.2 | 0.18 ± 0.05 | 1.9 ± 0.3 | 100.0 ± 1.2 |

TABLE 6-continued

| GROUP | TOTAL CELL CONCENTRATION ($\times 10^5$ cell/ml) | EOSINOPHIL CONCENTRATION ($\times 10^5$ cell/ml) | EOSINOPHIL RATIO (%) | EOSINOPHIL SUPPRESSION RATE (%) |
|---|---|---|---|---|
| 0.5 mg GROUP | 18.7 ± 2.1 | 3.29 ± 0.54 | 17.2 ± 2.0** | 24.7 ± 13.2 |
| 1.0 mg GROUP | 19.4 ± 1.6 | 3.35 ± 0.35 | 17.6 ± 1.9* | 23.2 ± 8.5 |
| 2.0 mg GROUP | 15.8 ± 1.7 | 2.48 ± 0.35* | 16.2 ± 1.6** | 44.3 ± 8.6* |

Average values ± standard error.
n = 9 for the control group only,
n = 10 for the other groups.
*, **p < 0.05, 0.01 (vs. control group, Dunnett's multiple comparison test).
Cell concentrations indicate the concentration in collected peritoneal fluid.

INDUSTRIAL APPLICABILITY

The present invention provides novel agents for preventing and/or treating allergies. These agents for preventing and/or treating allergies include dietary compositions for preventing and/or treating allergies through addition of an effective amount to powdered milk for infants, health-promoting food, or food for sick people.

The invention claimed is:

1. A dietary composition or drink comprising a biologically pure culture of *Lactobacillus gasseri* OLL2809 deposited under the accession number NITE BP-72 that is in a concentrated form or a dried form, at a content of 0.001% (w/w) or higher, wherein the concentrated form contains $4 \times 10^{10}$ cells/g or higher of said *Lactobacillus gasseri* OLL2809, or the dried form contains $5 \times 10^{11}$ cells/g or higher of said *Lactobacillus gasseri* OLL2809.

2. The dietary composition of claim 1, which comprises a formula milk for infants, food for infants, food for nursing women, health-promoting food, food for people with allergic symptoms, or fermented milk.

* * * * *

UNITED STATES PATENT AND TRADEMARK OFFICE
CERTIFICATE OF CORRECTION

PATENT NO. : 9,314,041 B2  
APPLICATION NO. : 11/817617  
DATED : April 19, 2016  
INVENTOR(S) : Toshihiro Sashihara Page 1 of 1

It is certified that error appears in the above-identified patent and that said Letters Patent is hereby corrected as shown below:

Claims

<u>Column 22,</u>
Line 21, claim 2, "The dietary composition of claim 1" should read --The dietary composition or drink of claim 1--.

Signed and Sealed this
Nineteenth Day of July, 2016

Michelle K. Lee
*Director of the United States Patent and Trademark Office*